(12) United States Patent
Thacker et al.

(10) Patent No.: US 8,295,945 B1
(45) Date of Patent: *Oct. 23, 2012

(54) NEURAL STIMULATION LEAD FIXATION

(75) Inventors: James R. Thacker, Eureka, MO (US); Michael S Colvin, Newbury Park, CA (US); David K. L. Peterson, Saugus, CA (US); James P. McGivern, Wake Forest, NC (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 1075 days.

This patent is subject to a terminal disclaimer.

(21) Appl. No.: 11/464,109

(22) Filed: Aug. 11, 2006

Related U.S. Application Data

(63) Continuation-in-part of application No. 10/155,146, filed on May 24, 2002, now Pat. No. 7,099,718.

(60) Provisional application No. 60/294,283, filed on May 29, 2001.

(51) Int. Cl.
*A61N 1/05* (2006.01)

(52) U.S. Cl. .......................................... 607/117; 607/118

(58) Field of Classification Search .......... 607/129–131, 607/116–117
See application file for complete search history.

(56) References Cited

U.S. PATENT DOCUMENTS

| | | | |
|---|---|---|---|
| 3,646,940 A | 3/1972 | Timm et al. | |
| 3,724,467 A | 4/1973 | Avery et al. | |
| 3,822,708 A | 7/1974 | Zilber | |
| 3,994,302 A | 11/1976 | Brennen | |
| 4,282,886 A * | 8/1981 | King | 607/130 |
| 4,338,945 A | 7/1982 | Kosugi et al. | |
| 4,379,462 A | 4/1983 | Borkan et al. | |
| 4,418,697 A | 12/1983 | Tama | |
| 4,519,403 A | 5/1985 | Dickhudt | |
| 4,706,688 A | 11/1987 | Michael et al. | |
| 4,809,712 A | 3/1989 | Kuzma | |
| 4,923,469 A | 5/1990 | Frachet et al. | |
| 4,983,167 A | 1/1991 | Sahota | |
| 5,056,532 A * | 10/1991 | Hull et al. | 607/124 |
| 5,121,754 A | 6/1992 | Mullett | |
| 5,277,199 A | 1/1994 | DuBois et al. | |
| 5,417,719 A | 5/1995 | Hull et al. | |

(Continued)

OTHER PUBLICATIONS

U.S. Appl. No. 10/155,146, Official Communication mailed Apr. 27, 2005 (11 pages).

(Continued)

*Primary Examiner* — Niketa Patel
*Assistant Examiner* — Joseph Stoklosa
(74) *Attorney, Agent, or Firm* — Frommer Lawrence & Haug LLP; Bruce E. Black

(57) ABSTRACT

An implantable lead having at least one electrode contact at or near its distal end prevents undesirable movement of the electrode contact from its initial implant location. One embodiment relates to a spinal cord stimulation (SCS) lead. A first injectable material is injected into the dura space to mechanically position the electrode array with respect to the spinal cord. Conjunctively for use with adhesives, or alternatively for use instead of the adhesives, a balloon may be positioned on the electrode lead array. The balloon is filled with air, liquid or a compliant material. When inflated, the balloon stabilizes the lead with respect to the spinal cord and holds the lead in place. An elastic aspect of the balloon serves as an internal contained relief valve to limit the pressure the balloon may place on the surrounding tissues when the epidural space is constrained.

27 Claims, 5 Drawing Sheets

U.S. PATENT DOCUMENTS

| | | | |
|---|---|---|---|
| 5,489,294 | A | 2/1996 | McVenes et al. |
| 5,501,703 | A | 3/1996 | Holsheimer et al. |
| 5,573,007 | A * | 11/1996 | Bobo, Sr. .................. 600/561 |
| 5,597,381 | A | 1/1997 | Rizzo, III |
| 5,733,322 | A | 3/1998 | Starkebaum |
| 5,935,155 | A | 8/1999 | Humayun et al. |
| 6,002,956 | A * | 12/1999 | Schaer ..................... 600/381 |
| 6,038,484 | A | 3/2000 | Kuzma |
| 6,144,883 | A | 11/2000 | Kuzma |
| 6,195,586 | B1 | 2/2001 | Kuzma |
| 6,240,322 | B1 * | 5/2001 | Peterfeso et al. ......... 607/126 |
| 6,319,241 | B1 | 11/2001 | King et al. |
| 6,329,337 | B1 * | 12/2001 | Morita et al. ............. 514/15.2 |
| 6,477,427 | B1 | 11/2002 | Stolz et al. |
| 6,510,347 | B2 * | 1/2003 | Borkan ..................... 607/117 |
| 6,795,737 | B2 | 9/2004 | Gielen et al. |
| 7,099,718 | B1 * | 8/2006 | Thacker et al. ........... 607/117 |
| 7,856,277 | B1 * | 12/2010 | Thacker et al. ........... 607/117 |
| 7,983,766 | B1 * | 7/2011 | Thacker et al. ........... 607/117 |
| 2002/0165593 | A1 * | 11/2002 | Hayashi et al. ............ 607/88 |

OTHER PUBLICATIONS

U.S. Appl. No. 10/155,146, Official Communication mailed Nov. 28, 2005 (10 pages).

U.S. Appl. No. 10/155,146, Official Communication mailed Sep. 1, 2005 (10 pages).

U.S. Appl. No. 11/464,128, Official Communication mailed Dec. 10, 2008 (17 pages).

U.S. Appl. No. 11/464,137 Official Communication mailed Feb. 25, 2009, 10 pgs.

U.S. Appl. No. 11/464,128, Official Communication Mailed Jun. 11, 2009.

U.S. Appl. No. 11/464,137 Official Communication Mailed Jul. 6, 2009.

U.S. Appl. No. 11/464,128 Official Communication Mailed Aug. 19, 2009.

U.S. Appl. No. 11/464,137, Official Communication mailed Sep. 19, 2008.

Official Communication, U.S. Appl. No. 11/464,137, mail date Dec. 29, 2009.

Official Communication, U.S. Appl. No. 11/464,128, mailed May 26, 2010.

Official Communication, U.S. Appl. No. 11/464,128, mailed Nov. 8, 2010.

* cited by examiner

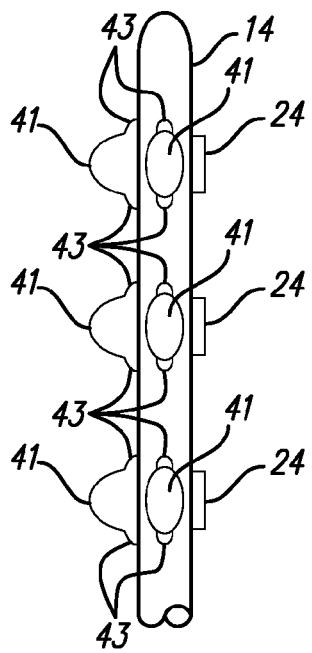
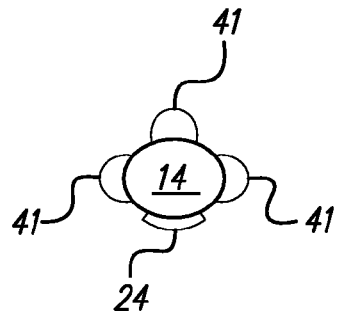
FIG. 4
FIG. 4A
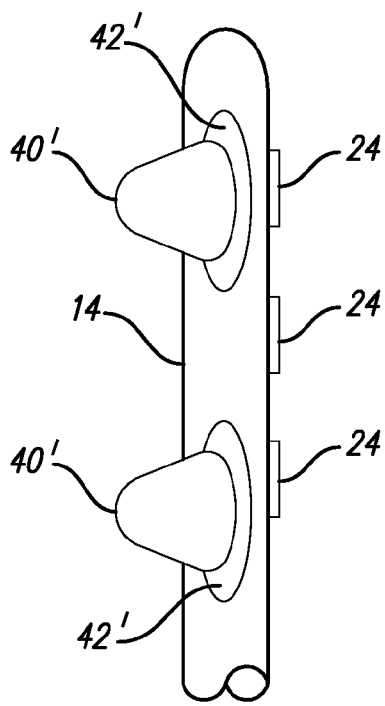
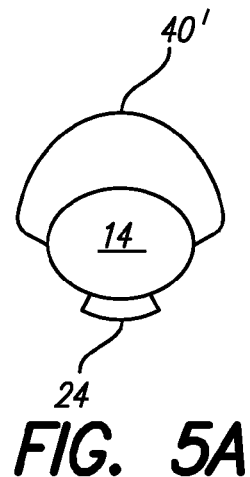
FIG. 5
FIG. 5A

NEURAL STIMULATION LEAD FIXATION

The present application is a Continuation-in-Part of U.S. application Ser. No. 10/155,146, filed May 24, 2002; which claims the benefit of U.S. Provisional Application Ser. No. 60/294,283, filed May 29, 2001, which applications are incorporated herein by reference.

BACKGROUND OF THE INVENTION

The present invention relates to a neural stimulation systems, e.g., a spinal cord stimulation system. More particularly, the invention relates to neural stimulation leads that include lead fixation means, i.e., ways to assure that the lead, once implanted, does not move away from its desired implant location.

Spinal cord stimulation (SCS) is a well accepted clinical method for reducing pain in certain populations of patients. SCS systems typically include an implanted pulse generator, lead wires, and electrodes connected to the lead wires. The pulse generator generates electrical pulses that are delivered to the dorsal column fibers within the spinal cord through the electrodes which are implanted along the dura of the spinal cord. In a typical situation, the attached lead wires exit the spinal cord and are tunneled around the torso of the patient to a sub-cutaneous pocket where the pulse generator is implanted.

When an electrical pulse, or sequence of pulses, is applied to a selected electrode, or combination of electrodes, the patient typically experiences a "paresthesia" (usually manifest as a mild tingling sensation) that is therapeutic, i.e., that relieves the pain, or other discomfort, the patient is experiencing, or that otherwise aids the patient in some useful way.

Spinal cord and other stimulation systems are known in the art. For example, in U.S. Pat. No. 3,646,940, there is disclosed an implantable electronic stimulator that provides timed sequenced electrical impulses to a plurality of electrodes so that only one electrode has a voltage applied to it at any given time. Thus, the electrical stimuli provided by the apparatus taught in the '940 patent comprise sequential, or non-overlapping, stimuli.

In U.S. Pat. No. 3,724,467, an electrode implant is disclosed for the neuro-stimulation of the spinal cord. A relatively thin and flexible strip of physiologically inert plastic is provided with a plurality of electrodes formed thereon. The electrodes are connected by leads to an RF receiver, which is also implanted, and which is controlled by an external controller. The implanted RF receiver has no power storage means, and is coupled to the external controller in order for neuro-stimulation to occur.

In U.S. Pat. No. 3,822,708, another type of electrical spinal cord stimulating device is shown. The device has five aligned electrodes which are positioned longitudinally on the spinal cord and transversely to the nerves entering the spinal cord. Current pulses applied to the electrodes are said to block sensed intractable pain, while allowing passage of other sensations. The stimulation pulses applied to the electrodes are approximately 250 microseconds in width with a repetition rate of from 5 to 200 pulses per second. A patient-operable switch allows the patient to change which electrodes are activated, i.e., which electrodes receive the current stimulus, so that the area between the activated electrodes on the spinal cord can be adjusted, as required, to better block the pain.

Other representative patents that show spinal cord stimulation systems or electrodes include U.S. Pat. Nos. 4,338,945; 4,379,462; 4,519,403; 5,121,754; 5,417,719 and 5,501,703, incorporated herein by reference.

The '403 patent teaches a balloon lead and inflator. However, the '403 patent does not teach the use of a safety valve to release pressure that might build up, or otherwise be present, when such lead is used.

U.S. Pat. No. 5,733,322, also incorporated herein by reference, discloses a positive fixation percutaneous epidural neurostimulation lead that utilizes an extension that extends distally beyond the most distal electrode. The extension is held in place by contact with both the dura and spinal canal wall so that lateral lead migration of the electrodes is minimized. Other electrode fixation techniques are taught, e.g., in U.S. Pat. No. 4,418,697, which describes an adhesive (putty) to fixate electrodes to the skin; and in U.S. Pat. No. 4,282,886, which describes an adhesive adapted to attach an electrode to the epicardium. Both the '697 and the '886 patents are likewise incorporated herein by reference.

Disadvantageously, when a neural stimulation lead chronically or temporarily moves, the ramifications to the patient are multifold. For example, an SCS lead that moves up, down or rotates to the side of the spinal cord can result in therapy no longer being adequate to attain the desired paresthesia, thereby rendering the SCS system incapable of performing its intended function. On a temporary basis, the lead can move, which movement may thereafter require patient adjustment of the stimulation energy, e.g., to reduce the stimulation output or increase the stimulation output, and in some instances such adjustment of the stimulation energy may not be possible, thereby again rendering the SCS system ineffective for its intended purpose.

Thus, it is seen that maintaining the correct lead position is critical, and an undesirable movement of the lead can render the SCS, or other neural stimulation system, ineffective and useless. Moreover, as the correct lead position is maintained, appropriate safeguards should exist to prevent excessive compression of the spinal cord. What is needed are mechanisms built into the lead design that: (1) acutely fixate the lead to its desired location, e.g., to the dura in the case of an SCS system, to thereby allow scare maturation to occur (which scare maturation will thereafter permanently maintain the lead in its desired location); or (2) permanently fixate the lead in its desired location from the onset of implantation; and (3) limit compression on the spinal cord.

SUMMARY OF THE INVENTION

The teachings of the present disclosure address the above and other needs by providing an implantable neural lead having an electrode array at or near its distal end that prevents undesirable movement of the electrode array from its initial implant location by filling the space that surrounds the lead into which the lead could otherwise move, and/or that adheres, i.e., "glues", the electrode array to its desired implant location.

In the case of an SCS lead, movement of the lead array is predominately caused due to the geometry of the epidural space. That is, the epidural space allows the spinal cord to independently move with respect to the vertebra, disks and ligaments which comprise the structural support of the spine. In one embodiment of the present disclosure, a first injectable material that adheres to the dura is injected into the dura space to mechanically position the electrode array with respect to the spinal cord. This first adhering material is introduced through the lumen of the lead array. An orifice to the lumen, which may be marked with a radio opaque marker, is located on the side of the lead where the attachment is to occur so that the adhering material is emitted from the lead tangential to the lead body at the level of the stimulating electrodes. By way of example, the first adhering material may be selected from the group that includes cyanoacrylate, fibrin, reconstituted collagen, polyethylene glycol, and polyacrylamide. Other examples of adhering materials that may be used include aldehyde (e.g. glutaraldehyde or formaldehyde), cross-linked natural proteins (e.g. collagen or albumin), chitosan adhesives (mussel glue), and photocurable adhesives (e.g., silicones, acrylates, polysaccharides, proteins, etc.).

In a second embodiment, used in conjunction with or as an alternative to the first embodiment, a balloon is positioned on the electrode lead array. Such balloon runs along the axis of the lead at the stimulating electrode level and encompasses a significant portion, e.g., 180 degrees, of the arc when a cross section of the lead is viewed. The balloon is filled with air, liquid or a compliant material. When inflated, the balloon stabilizes the lead with respect to the spinal cord. The pressure of the balloon is monitored or otherwise controlled during the filling process in order to determine at what point the filling process should be discontinued. The balloon may be segmented into several balloon compartments, each having different dilated balloon diameters to account for different geometry between and within a given patient. An elastic aspect of the balloon serves as an internal contained relief valve to limit the pressure the balloon may place on the surrounding tissues when the epidural space is constrained.

In accordance with one aspect of the present disclosure, an implantable lead is thus provided that is fixed to its desired implant location.

In accordance with another aspect of the present disclosure, a lumen within the lead, used to allow a removable stylet to help place and position an electrode array at or near a distal end of the lead during the implant process, may also be used as the channel through which the first adhering material is dispensed. Such dispensing may occur either through insertion of a cannula within the lumen (followed by dispensing the first adhering material within the cannula) or direct injection of the first adhering material into the lumen. Additionally, in one embodiment such channel further serves as a fluid inlet (where "fluid" is used here in its broad sense to mean either a liquid or a gas) through which a balloon formed in the lead near or at the location of the electrode array may be inflated to a desired size and/or pressure. In another embodiment, a separate fluid channel may be formed through the lead body through which the balloon may be inflated. In yet another embodiment, the first adhering material also functions as the fluid that inflates the balloon(s).

In accordance with still a further aspect of the present disclosure, the lead includes an implanted pressure release mechanism to ensure that there is not excessive compression placed on the spinal cord by the implantable lead.

BRIEF DESCRIPTION OF THE DRAWINGS

The above and other aspects, features and advantages of the teachings of the present disclosure will be more apparent from the following more particular description thereof, presented in conjunction with the following drawings wherein:

FIG. 3A is a sectional view of the array shown in FIG. 3 taken along the line 3A-3A, and illustrates the balloon in both an inflated and deflated condition;

FIG. 3B is a sectional view of the array shown in FIG. 3 taken along the line 3B-3B, and illustrates the balloon in an inflated condition;

FIGS. 4 and 4A depict an alternative embodiment wherein a series of side lobe balloons are employed with an electrode array;

FIGS. 5 and 5A similarly show an alternative embodiment wherein a series of lateral stabilizing balloons are employed with the electrode array.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

At the outset, it should be noted that the teachings of the present disclosure are directed to the fixation of implantable leads, such as neural stimulation leads or cardiac leads, and more particularly to the fixation of electrodes, or electrode arrays, attached to neural stimulation leads or cardiac leads so that such electrodes, or electrode arrays, remain in a desired position relative to the tissue that is to be stimulated. For purposes of the present disclosure, the terms "lead" and "electrode" and "electrode array" may thus be used interchangeably, unless the context clearly indicates otherwise. That is, while the narrow purpose of the present discloure is to fix the electrodes relative to the tissue to be stimulated, in describing such purpose other terminology may be used, such as fixing the lead, or fixing the electrode array.

It should further be noted that the principles and teachings of the present disclosure may be used with any kind of neural stimulation lead, or cardiac lead, particularly those that are implanted within a tissue cavity (the presence of which cavity allows undesirable movement of the lead). Thus, while the present disclosure will be described in terms of a spinal cord stimulation (SCS) lead adapted for implantation in the epidural space next to the spine, it is to be understood that such description is intended to be only exemplary and not limiting. The scope of the present disclosure is determined by the claims.

Figure 1:
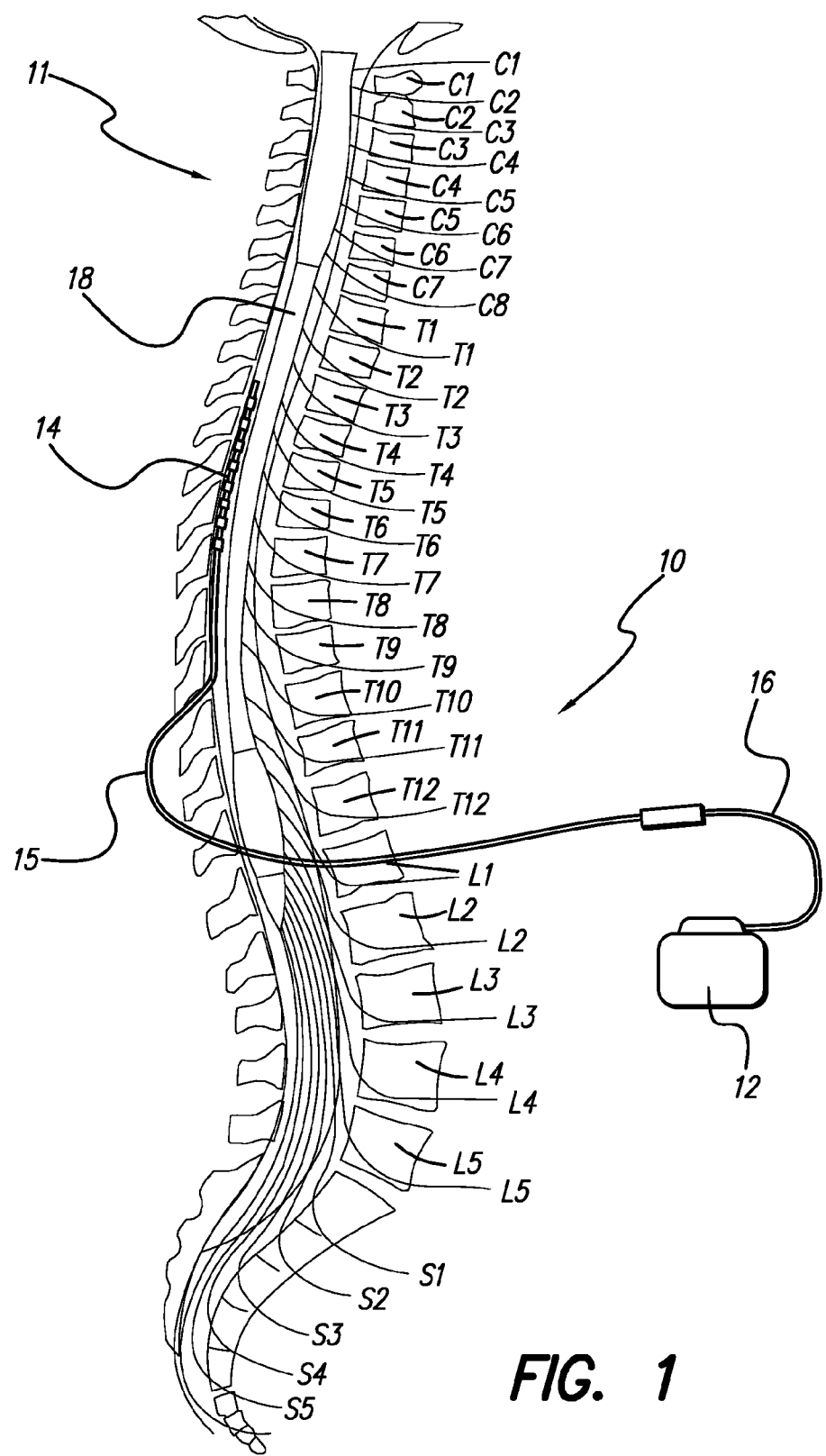
FIG. 1 illustrates a representative spinal cord stimulation system implanted in a patient.

Turning first to FIG. 1, there is shown a representative SCS system 10 implanted in a patient 11. The SCS system 10 is used typically to treat chronic pain by applying electrical stimulation pulses to selected locations along the spine. The SCS system 10 includes an Implantable Pulse Generator (IPG) 12 that generates the electrical stimulation pulses used for stimulation. An electrode array 14 at or near the distal end of an implanted stimulation lead 15 is inserted into the epidural space next to the spinal cord 18. As required, depending upon the location where the IPG 12 is implanted, a lead extension 16 may be used to connect the lead 15 (and hence the electrode array 14) to the IPG. The electrical stimulation provided by the IPG 12, when properly performed, has the effect of blocking sensed pain while not interfering with other nerve functions. The present disclosure relates to the electrode array 14 and the manner used to fix the location of the electrode array 14 relative to the spinal cord 18.

Figure 2:
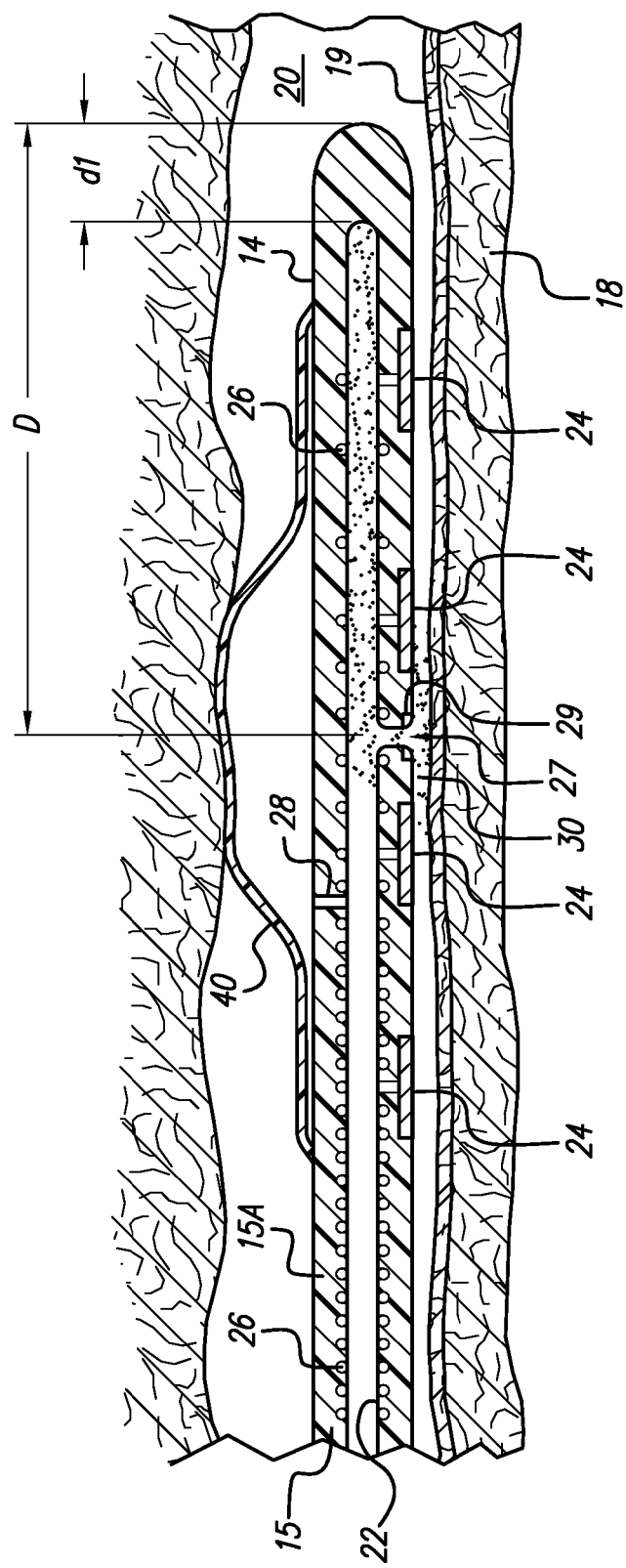
FIG. 2 is a sectional view that depicts the electrode array as taught by the present disclosure implanted adjacent the spine.

FIG. 2 schematically illustrates a sectional view of the epidural space 20 adjacent the spinal cord 18 into which the implantable lead 15, and more particularly the electrode array 14 at the distal end of the lead 15, of the present disclosure is implanted. As seen in FIG. 2, the electrode array 14 typically includes a multiplicity of spaced-apart electrode contacts 24. Such electrode contacts 24 may reside along one side of the array 14, or may be bands that encircle a body 15A of the lead 15. Each electrode contact 24 is electrically connected to a respective wire 26 that is embedded, or otherwise located within, the body 15A of the lead 15. For the example shown in FIG. 2, the wires 26 are helically wound, thereby allowing the lead 15 to readily flex and bend. The inside of the helically wound wires 26 defines a lumen 22 that passes longitudinally through the body of the lead. A proximal end of the wires 26 (not shown in FIG. 2) connects to the IPG 12 either directly or through an extension lead 16 (FIG. 1). It is to be understood that a lead having helically-wound wires 26 therein represents only one way in which an implantable neural stimulation lead may be formed. Any method known in the art, or yet to be developed in the art, for electrically connecting an electrode contact 24 to an implantable pulse generator may be used with the present disclosure.

The body 15A of the lead 15 may be made from any suitable biocompatible material, such as silicone or Silastic or other compliant material, as is known in the art, or as will yet be developed in the art. The body 15A of the lead 15 may also be referred to as a flexible carrier on which the spaced-apart electrode contacts 24 are carried.

At least one orifice 27 is formed in the body 15A of the array 14 near the electrode contacts 24. The location of the orifice 27 along the lead body 15A may be marked with a radio opaque marker 29. It is through this orifice 27 that a first adhering material 30, e.g., an adhesive, may be dispensed through the lumen 22 of the lead 15 to the area where the electrode array 14 is to be attached, e.g., adhered or glued, to the spinal cord 18. (This adhering material 30 is represented in FIG. 2 by closely spaced small dots.)

Rather than dispensing the adhesive through a lumen 22 that passes through the lead body, it is also possible, in accordance with an alternative embodiment of the teachings of the present disclosure, to provide a cannula, or similar tubing, that passes along one side of the lead body, e.g., parallel to the flexible carrier, with an opening or orifice near the electrode contacts.

It should be noted that the adhesive may have properties that cause it to adhere to the body tissue and to (1) the electrode contacts 24, or (2) insulative material separating the electrode contacts, or (3) both the electrode contacts 24 and the insulative materials separating the electrode contacts. In some embodiments of an implantable lead, in the region near the electrode contacts 24, the electrode contacts are separated by insulative material, which is non-conductive. Thus, for purposes of maintaining or holding the position of the electrode contacts near or against the tissue to be stimulated, it matters little whether the adhesive bonds with the electrode contacts, and/or with the insulative material that separates or insulates the electrode contacts from each other, or other insulative material, in the vicinity of the electrode contacts. However, as discussed below, it is generally preferable that the adhesive not bond with a compliant material, i.e., that it not bond with silicone or other material from which the lead body 15A is made. Thus, in most instances, except when an insulative or other material is used near the electrodes that is different from silicone, or other material from which the lead body is made, the adhesive bonds with the electrode contacts and with the surrounding tissue.

The adhering material 30 has properties that allow it to be injected through the lumen 22 and orifice 27 of the lead 15. Additionally, the material 30 should have properties that cause it to adhere to the dura 19 (an outer layer that surrounds the spinal cord 18) and the electrode contacts 24, but which do not cause it to adhere to the dura space lining or a compliant material (e.g., the silicone or other material from which the lead body 15A is made). By way of example, the first adhering material 30 may be selected from the group that includes cyanoacrylate, fibrin, reconstituted collagen, polyethylene glycol, and polyacrylamide. Other examples of adhering materials that may be used include aldehyde (e.g. glutaraldehyde or formaldehyde), cross-linked natural proteins (e.g. collagen or albumin), chitosan adhesives (mussel glue), and photocurable adhesives (e.g., silicones, acrylates, polysaccharides, proteins, etc.).

It is thus seen that the teachings of the present disclosure addresses the use of an adhesive to fix the actual electrode itself to the tissue. On exemplary embodiment contemplates injecting the adhesive through the lumen 22 and orifice 27 of the lead 15. However, other techniques may also be used, particularly for other types of lead and electrode configurations. For example, the adhesive may be placed prior to, during or after the implantation of the electrode(s). The adhesive is formulated to be gentle to the tissue, but assures that the electrode(s) remain in the desired proper location and orientation because the fixation is on the electrode itself. The adhesive may be used in conjunction with traditional methods, e.g., fixation at a distance. The adhesive may also be made soft or hard, permanent or temporary, and can be made to be biocompatible. The adhesive may be synthetic, e.g., cyanoacrylate, or it may be a substance that is natural to the body, e.g., fibrin glue.

Returning to FIG. 2, it is further seen in FIG. 2, the electrode array 14 also includes a balloon 40 that, when inflated, fills the remaining epidural space 20 surrounding the electrode array 14 and lead 15. Further details relating to the balloon 40 are discussed below in conjunction with the description of FIGS. 3-5. While both the balloon 40 and adhesive 30 are illustrated as being used in connection with the same lead 15 in FIG. 2, such conjunctive use is only exemplary. In some instances, only the adhesive 30 need be used to fix the electrode contacts to a desired location. In other instances, only the balloon 40 need be used.

Typically, after removal of the stylet from the lumen 22, the adhering material 30 is injected into the lumen 22. As it is injected, it fills the distal end of the lumen first, and then exits out the orifice 27 into the space adjacent the spinal cord 18 where the adhesion occurs between the dura 19 and electrode contacts 24. Because the volume of the lumen at the distal end of the lead up to the location of the orifice 27 is known, or can be readily calculated (i.e., the orifice 27 is a known distance D from the tip of the electrode array 14, and the distance d1 from the tip to the beginning of the lumen 22 is also known or can be readily estimated; thus, the approximate volume of the lumen 22 up to the location of the orifice 27 can be determined), a desired amount (volume) of material 30 to be injected through the lumen 22 can be determined.

After the proper amount, e.g., volume, of adhesive or other adhering material 30 has been injected into the lumen 22, a second material, e.g., a gas, such as air, or a liquid which does not mix with the first material 30, may also be injected into the lumen 22, forcing the first adhering material 30 to the distal end of the lumen, and through the first orifice 27, as desired.

This second material may then pass through a second orifice 28 in order to inflate the balloon 40 to a desired pressure. Alternatively, where the first material 30 does not readily adhere to compliant materials, such as the materials from which the body 15A of the lead 15 is made, and from which the balloon 40 is made, the first material 30 may, in addition to being injected through the orifice 27 in order to adhere the dura 19 to the electrode contacts 24, also be used as the substance that inflates the balloon 40 to a desired pressure. As a still further means of inflating the balloon, the balloon 40 may be inflated to a desired pressure and/or volume by injecting an inflating material, e.g., a saline solution, through a separate channel 25 apart from the lumen 22, as shown in FIG. 3B, discussed below.

Figure 3:
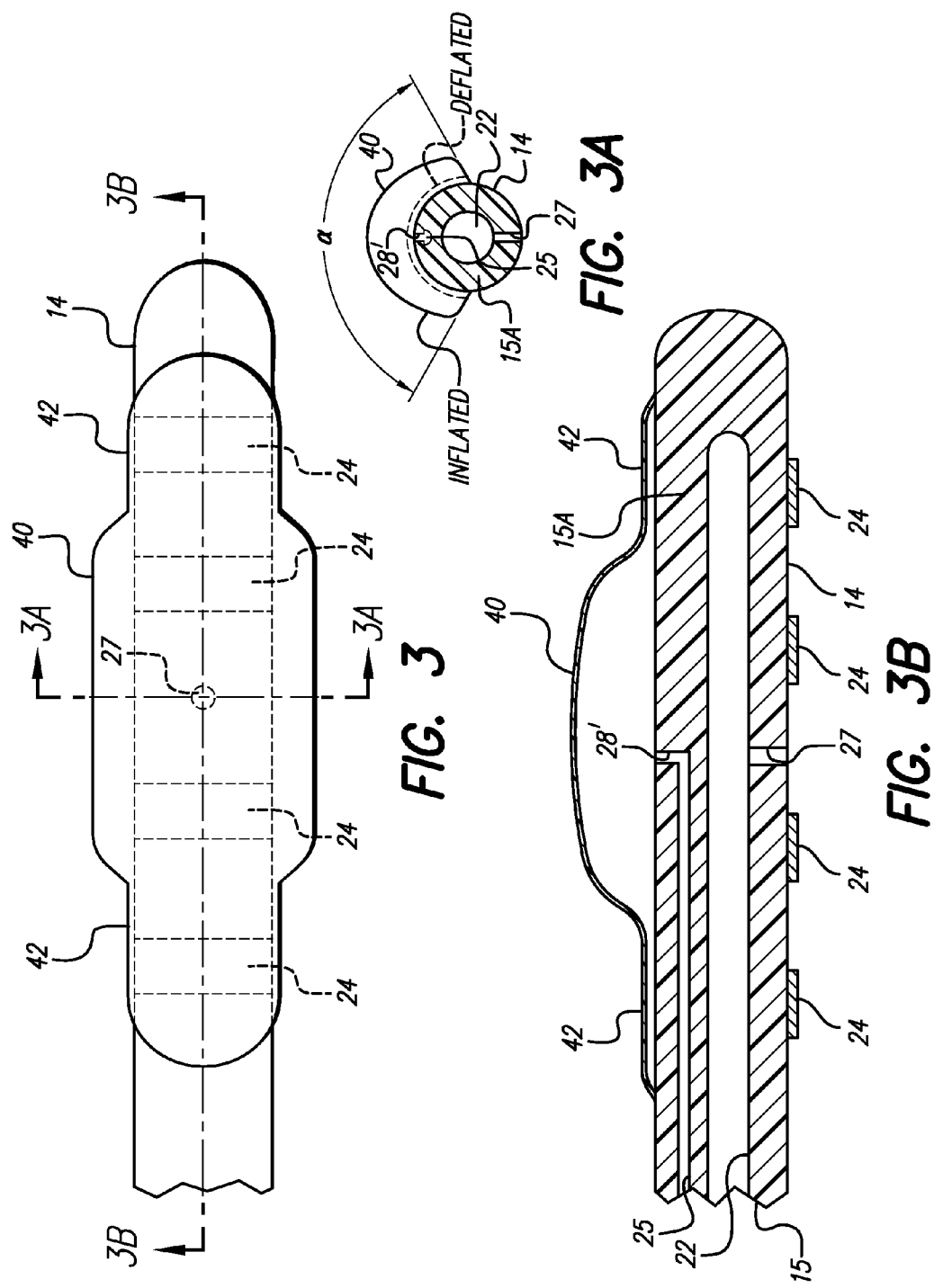
FIG. 3 is a first side view of the electrode array as taught by the present disclosure, with the balloon inflated, as viewed while looking at the back side of the array, i.e., that side opposite from the orifice through which an adhering material may be dispensed.

Turning next to FIGS. 3, 3A and 3B, further details associated with one embodiment of the electrode array 14 of the present disclosure are illustrated. FIG. 3 is a first side view of the electrode array 14, with the balloon 40 inflated, as viewed while looking at the back side of the array, i.e., that side opposite from the orifice 27 through which the adhering material 30 is dispensed. FIG. 3A is a sectional view of the array shown in FIG. 3 taken along the line 3A-3A, and illustrates the balloon 40 in both an inflated and deflated condition. FIG. 3B is a sectional view of the array shown in FIG. 3 taken along the line 3B-3B, and illustrates the balloon 40 in an inflated condition. As seen in FIGS. 3, 3A and 3B, the orifice 27 through which the adhering material is dispensed is located near the electrode contacts 24. The balloon 40 inflates around the portion of the electrode array 14 where the electrode contacts 24 are located. As seen best in the cross-sectional view of the lead 15 shown in FIG. 3A, the balloon 40 encircles the lead 14 over an angle α. The angle α will typically range from about 20 to 180 degrees, but may, in some embodiments, range from about 20 to 270 degrees.

For the exemplary embodiment shown in FIGS. 3, 3A and 3B, the balloon 40 is inflated through a channel 25 and orifice 28' that is separate from the lead lumen 22 and orifice 27. When the balloon 40 is inflated, some means for monitoring the injected material pressure so as to determine an appropriate point at which the inflation should terminate may be used. Such means may be simply injecting a known volume of inflating fluid. Alternatively, a pressure gauge may be used in conjunction with the inflating process so that the pressure of the inflating fluid can be accurately measured.

Also, for the exemplary embodiment shown in FIGS. 3, 3A and 3B, the balloon 40 includes sections 42 that have different elastic properties than the main balloon portion, e.g., are made so as to have a thicker wall than the main balloon portion. Thus, these balloon sections 42 require more pressure to inflate. As such, the balloon portions 42 function as an internal contained relief valve to limit the pressure the balloon 40 may place on the surrounding tissue when the epidural space is constrained (which may occur, for example, when the patient bends his back or spine). Limiting the pressure that the balloon 40 can impart to the surrounding tissue through use of such internal contained relief values 42 helps assure that the patient will not experience any undue discomfort as he or she moves about. In this way, excessive compression on the spinal cord is avoided.

Next, with reference to FIGS. 4 and 4A, an alternative exemplary embodiment is illustrated wherein a sequence of lobe balloons 41 are employed with an electrode array 14. Such embodiment includes a sequence of three lobe balloons 41 for each electrode contact 14. Such number of lobe balloons in each sequence is only exemplary. Further, while the embodiment shown in FIGS. 4 and 4A has one sequence of lobe balloons associated with each electrode contact, it is also possible to have a sequence of lobe balloons associated with only selected electrode contacts, e.g., a most distal electrode contact, a most proximal electrode contact, and/or a middle electrode contact. The lobe balloons 41 are inflated through the longitudinal lumen 22. When inflated, the lobe balloons 41 engage the tissue surrounding the distal end of the implanted neural lead 15 and secure the electrode array 14 to the tissue within which it is implanted. Each lobe balloon 41 includes an internal pressure relief portion 43.

Further, with reference to FIGS. 5 and 5A, yet another exemplary embodiment is depicted wherein a series of lateral stabilizing balloons 40' are employed with the electrode array 14. Each stabilizing balloon 40' includes an internal pressure relief portion 42'. The number of lateral stabilizing balloons 40' will typically be at least two, and could be as many as four or five, or more, depending upon the length of the electrode array 14. The stabilizing balloons 40' are inflated through the longitudinal lumen 22. When inflated, the stabilizing balloons 40' engage the tissue surrounding the distal end of the implanted neural lead 15 and secure the electrode array 14 to the tissue within which it is implanted.

Figure 6:
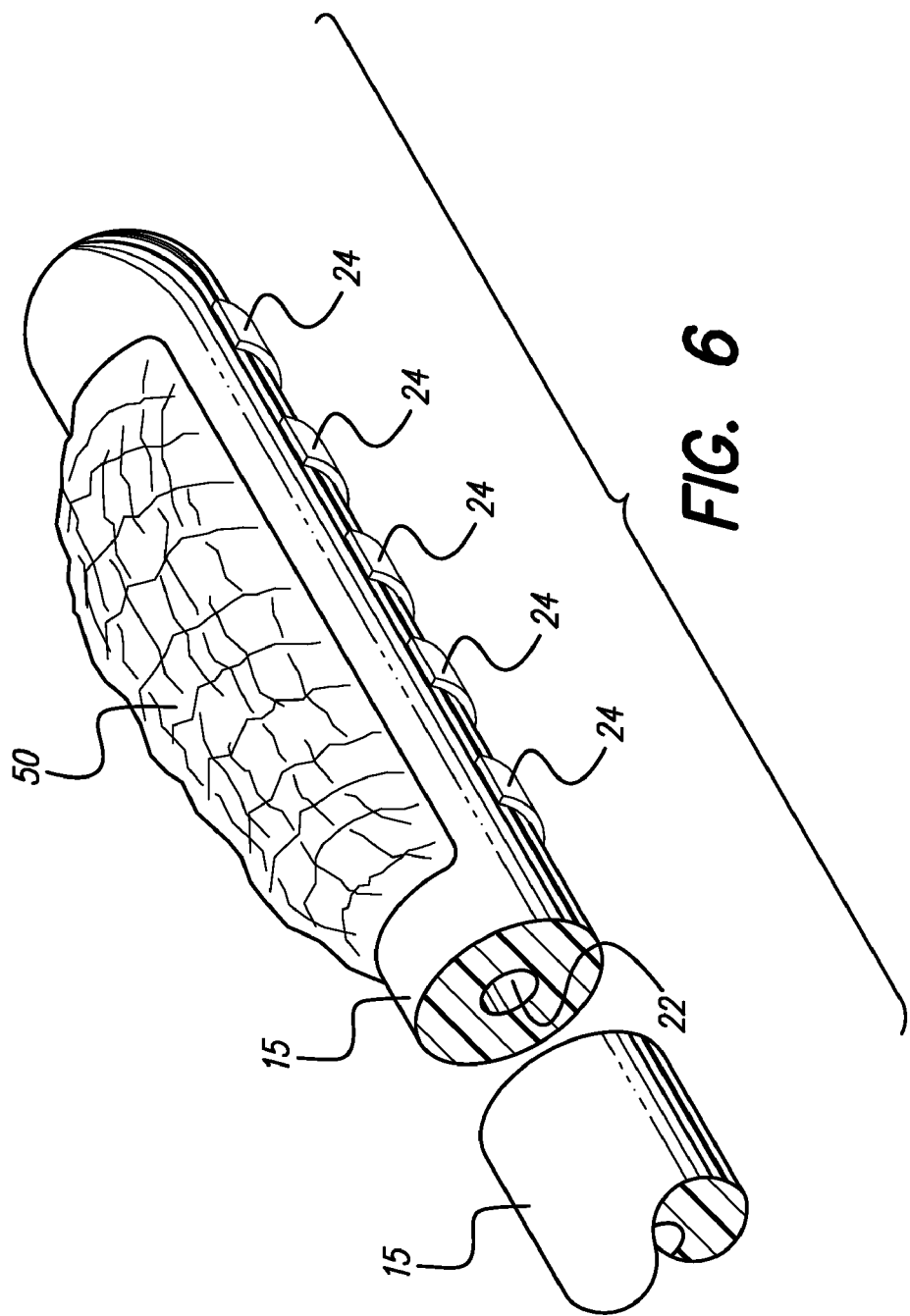
FIG. 6 shows another alternative embodiment wherein a spongy, flexible or compressive portion is employed with an electrode array.

In addition to the internal pressure relief portions 42 (FIGS. 3A, 3B), 42' (FIG. 5) and 43 (FIG. 4), which form part of the main balloon portion but with a thicker wall, other types of pressure relief mechanisms may be employed. For example, other highly compliant expandable positioning systems, such as foam, sponge or other lattice materials may also be employed. Indeed, the teachings of the present disclosure contemplates any pressure relief mechanism built into the lead that ensures excessive compression of the spine is avoided. Thus, as illustrated in FIG. 6, a spongy, flexible and/or compressible portion 50 is formed on the lead 15, opposite the electrodes 24. While the spongy, flexible and/or compressible portion 50 may be an elongate member, as shown in FIG. 6, it should also be understood that such portion(s) 50 may be at the same location and using the same or similar patterns, as are employed by the balloon portions previously described.

The portion 50 is made from a silastic spongy material that is both flexible and compressible. A suitable flexible and compressible material that may be used for the portion 50 is, e.g., polyurethane, or equivalents. The portion 50 may be fabricated as: (1) an open cell material that is collapsed through application of a vacuum on the lumen and/or implant insertion, with the vacuum being removed after insertion, allowing the open cell material to open from its collapsed state; or (2) a balloon filled with a foam, which foam is flexible and compressible. It is to be emphasized that any material that is compatible with body tissue and sufficiently flexible and compressible may be used for the portion 50, including materials that may not yet be developed.

While the invention herein disclosed has been described by means of specific embodiments and applications thereof, numerous modifications and variations could be made thereto by those skilled in the art without departing from the scope of the invention set forth in the claims.

What is claimed is:

1. An implantable lead comprising:
   a lead body;
   a lumen passing longitudinally through or along side the lead body;
   at least one electrode contact carried on the lead body at or near a distal end of the lead;
   means for making electrical contact with the at least one electrode contact from a proximal end of the lead;

a first orifice near the at least one electrode contact, wherein the first orifice provides fluid communication between the lumen and an exterior of the lead;

a first adhering material injectable through said lumen and first orifice to make contact with, and adhere said at least one electrode contact to, surrounding tissue;

an inflatable balloon integral with the lead body and opposite the first orifice, said inflatable balloon including an internal pressure relief portion; and a second orifice that fluidly connects the lumen with the inflatable balloon, wherein an inflating material may be injected into the balloon to inflate it through the lumen and second orifice, wherein said first adhering material and said inflating material comprise the same material.

2. The implantable lead of claim 1 wherein said first adhering material is selected from the group comprising cyanoacrylate, fibrin, reconstituted collagen, polyethylene glycol, polyacrylamide, aldehyde, cross-linked natural proteins, chitosan adhesives, and photocurable adhesives.

3. The implantable lead of claim 2 wherein the at least one electrode contact comprises a plurality of spaced-apart electrode contacts, and wherein the implantable lead is adapted to connect to a spinal cord stimulation system.

4. The implantable lead of claim 1 further including a second channel through the lead body that is separate and apart from the lumen, wherein said second channel is adapted to direct the inflating material into the balloon.

5. The implantable lead of claim 1 wherein the first adhering material is an adhesive.

6. The implantable lead of claim 5 wherein the adhesive is made hard.

7. The implantable lead of claim 5 wherein the adhesive is made soft.

8. The implantable lead of claim 5 wherein the adhesive is permanent.

9. The implantable lead of claim 5 wherein the adhesive is temporary.

10. The implantable lead of claim 5 wherein the adhesive is made from a synthetic material.

11. The implantable lead of claim 5 wherein the adhesive is made from a substance that is natural to the body.

12. The implantable lead of claim 5 wherein the adhesive is biocompatible and formulated to be gentle to body tissue.

13. The implantable lead of claim 1 wherein said first adhering material is selected from the group comprising cross-linked natural proteins and chitosan adhesives.

14. An implantable lead comprising:

a lead body;

a lumen passing longitudinally through or along side the lead body;

at least one electrode contact carried on the lead body at or near a distal end of the lead;

means for making electrical contact with the at least one electrode contact from a proximal end of the lead;

a first orifice near the at least one electrode contact, wherein the first orifice provides fluid communication between the lumen and an exterior of the lead;

a first adhering material injectable through said lumen and first orifice to make contact with, and adhere said at least one electrode contact to, surrounding tissue;

an inflatable balloon integral with the lead body and opposite the first orifice, said inflatable balloon including an internal pressure relief portion, wherein the inflatable balloon includes an inflatable first portion and an inflatable second portion, wherein the second portion comprises the internal pressure relief portion, and wherein the second portion has different elasticity properties than the first portion such that more pressure is required to begin inflating the second portion than is required to begin inflating the first portion, wherein the second portion of the inflatable balloon provides an internal contained relief valve that limits the pressure in the first balloon portion.

15. The implantable lead of claim 14 wherein the inflatable balloon covers an area at a distal end of said lead body that, when the lead body is viewed in cross section, extends over an angle α of between 20 to 270 degrees.

16. The implantable lead of claim 14 further including a series of inflatable lateral stabilizing balloons spaced apart along a distal portion of the lead body.

17. The implantable lead of claim 14 wherein said inflatable balloon comprises a sequence of inflatable lobes associated with selected electrode contacts.

18. The implantable lead of claim 17 wherein the number of inflatable lobes in each sequence of inflatable lobes is three.

19. The implantable lead of claim 14 further including a second orifice that fluidly connects the lumen with the inflatable balloon, wherein an inflating material may be injected into the balloon to inflate it through the lumen and second orifice.

20. The implantable lead of claim 19 wherein said first adhering material and said inflating material comprise the same material.

21. The implantable lead of claim 14 where the inflatable first and second portions of the inflatable balloon have inflatable walls made from the same material, and wherein, prior to inflation, the inflatable walls of the inflatable second portion are thicker than the inflatable walls of the inflatable first portion.

22. An implantable lead comprising:

a lead body;

a lumen passing longitudinally through or along side the lead body;

at least one electrode contact carried on the lead body at or near a distal end of the lead;

means for making electrical contact with the at least one electrode contact from a proximal end of the lead;

a first orifice near the at least one electrode contact, wherein the first orifice provides fluid communication between the lumen and an exterior of the lead;

a first adhering material injectable through said lumen and first orifice to make contact with, and adhere said at least one electrode contact to, surrounding tissue;

an inflatable balloon integral with the lead body and opposite the first orifice, said inflatable balloon including an internal pressure relief portion, wherein the inflatable balloon includes an inflatable first portion and an inflatable second portion, wherein the first and second portions of the inflatable balloon have inflatable walls made from a same material, and wherein, prior to inflation, the inflatable walls of the second portion are thicker than the inflatable walls of the first portion.

23. The implantable lead of claim 22 wherein the inflatable balloon covers an area at a distal end of said lead body that, when the lead body is viewed in cross section, extends over an angle α of between 20 to 270 degrees.

24. The implantable lead of claim 22 further including a series of inflatable lateral stabilizing balloons spaced apart along a distal portion of the lead body.

25. The implantable lead of claim 22 wherein said inflatable balloon comprises a sequence of inflatable lobes associated with selected electrode contacts.

26. The implantable lead of claim 25 wherein the number of inflatable lobes in each sequence of inflatable lobes is three.

27. The implantable lead of claim 22 further including a second orifice that fluidly connects the lumen with the inflatable balloon, wherein an inflating material may be injected into the balloon to inflate it through the lumen and second orifice.

* * * * *